United States Patent
Sood et al.

(10) Patent No.: US 12,121,560 B2
(45) Date of Patent: *Oct. 22, 2024

(54) METHODS AND COMPOSITIONS FOR MAINTAINING THE CONFORMATION AND STRUCTURAL INTEGRITY OF BIOMOLECULES

(71) Applicant: TissueGen, Inc., Dallas, TX (US)

(72) Inventors: Paul R. Sood, Dallas, TX (US); Alpeshkumar P. Patel, Sachse, TX (US); Jennifer Seifert, Little Elm, TX (US); Ryszard Zarzycki, Dallas, TX (US)

(73) Assignee: TissueGen, Inc., Irving, TX (US)

( * ) Notice: Subject to any disclaimer, the term of this patent is extended or adjusted under 35 U.S.C. 154(b) by 387 days.

This patent is subject to a terminal disclaimer.

(21) Appl. No.: 17/522,570

(22) Filed: Nov. 9, 2021

(65) Prior Publication Data

US 2022/0062370 A1 Mar. 3, 2022

Related U.S. Application Data

(63) Continuation of application No. 16/521,297, filed on Jul. 24, 2019, now Pat. No. 11,197,905, which is a continuation of application No. 15/653,414, filed on Jul. 18, 2017, now Pat. No. 10,363,281.

(60) Provisional application No. 62/363,593, filed on Jul. 18, 2016.

(51) Int. Cl.
| | |
|---|---|
| *A61K 38/00* | (2006.01) |
| *C08B 37/00* | (2006.01) |
| *C08B 37/02* | (2006.01) |
| *C08H 1/00* | (2006.01) |
| *C08H 1/06* | (2006.01) |
| *C08L 3/02* | (2006.01) |
| *C08L 5/00* | (2006.01) |
| *C08L 5/02* | (2006.01) |
| *C08L 5/04* | (2006.01) |
| *C08L 5/08* | (2006.01) |
| *C08L 5/12* | (2006.01) |
| *C08L 89/00* | (2006.01) |
| *C08L 89/06* | (2006.01) |

(52) U.S. Cl.
CPC .......... *A61K 38/00* (2013.01); *C08B 37/0006* (2013.01); *C08B 37/0021* (2013.01); *C08B 37/0084* (2013.01); *C08H 1/00* (2013.01); *C08H 1/06* (2013.01); *C08L 3/02* (2013.01); *C08L 5/00* (2013.01); *C08L 5/02* (2013.01); *C08L 5/04* (2013.01); *C08L 5/08* (2013.01); *C08L 5/12* (2013.01); *C08L 89/00* (2013.01); *C08L 89/06* (2013.01)

(58) Field of Classification Search
CPC .................................. A61K 38/00; C08L 5/00
See application file for complete search history.

(56) References Cited

U.S. PATENT DOCUMENTS

| | | | |
|---|---|---|---|
| 4,352,883 A | 10/1982 | Lim | |
| 5,032,401 A | 7/1991 | Jamas et al. | |
| 5,149,543 A | 9/1992 | Cohen et al. | |
| 5,482,927 A | 1/1996 | Maniar et al. | |
| 5,500,161 A | 3/1996 | Andrianov et al. | |
| 7,033,603 B2 * | 4/2006 | Nelson | A61P 27/06 |
| | | | 514/772.3 |
| 8,623,419 B2 | 1/2014 | Malakhov et al. | |
| 10,363,281 B2 | 7/2019 | Nelson et al. | |
| 11,197,905 B2 * | 12/2021 | Seifert | C08L 5/02 |
| 2003/0059402 A1 | 3/2003 | Jin et al. | |
| 2006/0193769 A1 | 8/2006 | Nelson et al. | |
| 2016/0090415 A1 | 3/2016 | Marquette et al. | |

FOREIGN PATENT DOCUMENTS

| | | |
|---|---|---|
| CA | 2703807 | 11/2011 |
| EP | 1344520 A1 | 10/2007 |
| EP | 2016938 A1 | 1/2009 |
| WO | 1998046212 A1 | 10/1998 |
| WO | 200110421 A1 | 2/2001 |
| WO | 2004056311 A2 | 7/2004 |
| WO | 2005004928 A2 | 1/2005 |
| WO | 2009132224 A2 | 10/2009 |
| WO | 2012068619 A1 | 5/2012 |

OTHER PUBLICATIONS

European Patent Office—Supplementary European Search Report pertaining to Application No. 17831719.4-1112, dated Mar. 17, 2020, 13 pages.

Wang et al., "Lyophilization of water-in-oil emulsions to prepare phospholipid-based anhydrous reverse micelles for oral peptide delivery", European Journal of Pharmaceutical Sciences, 2010, 9 pages.

* cited by examiner

*Primary Examiner* — Carlos A Azpuru

(74) *Attorney, Agent, or Firm* — Sunstein LLP

(57) ABSTRACT

A liquid ink composition includes a liquid phase and particles suspended in the liquid phase, the particles containing a target pharmaceutical or biological agent. The biological activity of the target pharmaceutical or biological agent is preserved upon suspension of the particles in the liquid phase. The liquid phase is capable of solidifying via a solidification process.

3 Claims, No Drawings

METHODS AND COMPOSITIONS FOR MAINTAINING THE CONFORMATION AND STRUCTURAL INTEGRITY OF BIOMOLECULES

CROSS-REFERENCE TO RELATED APPLICATIONS

This application is a continuation of U.S. patent application Ser. No. 16/521,297, filed on Jul. 24, 2019, which is a continuation of U.S. patent application Ser. No. 15/653,414 filed on Jul. 18, 2017, which claims priority to U.S. Provisional Patent Application No. 62/363,593, which was filed on Jul. 18, 2016. Each of the above-described references are hereby incorporated herein by reference in its entirety.

FIELD OF THE INVENTION

This application relates to protecting pharmaceutical or biological molecules from organic solvents and more particularly, but not by way of limitation, to protecting molecules whose function is dependent on primary, secondary, tertiary, and/or quaternary structure to achieve and maintain function. This invention applies to the fields of pharmaceutics, medical devices, drug delivery devices, tissue engineering, advanced or chronic wound healing, textiles, 2D and 3D printing, mesofabrication, fermentation, biotechnology, protein production, genetics, genomics, protiomics, metabolomics, and the like.

BACKGROUND

U.S. Pat. No. 6,596,296 provides for "a composition of at least one biodegradable polymer fiber wherein the fiber is composed of a first phase and a second phase, the first and second phases being immiscible, and wherein the second phase comprises one or more therapeutic agents." The immiscible phases allow for therapeutic agents incorporated into the composition to be partially protected from an adverse organic environment so as to maintain their biological function. However, the interface between the phases can be detrimental to the therapeutic agent and alter its function. Therefore, this invention proposes an improvement over and an expansion of this concept to allow for the protection of therapeutic agents in potentially damaging organic solvent environments.

SUMMARY

In some embodiments, a composition includes a solution containing a target pharmaceutical or biological agent, and a substrate that is soluble in the solution. The substrate is capable of being solidified via a solidification process and the solidification process causes the substance to become physically or chemically cross-linked, vitrified, or crystallized. During the solidification process, particles are formed containing the pharmaceutical or biological agent. The target pharmaceutical or biological agent is located within the particles and retains proper conformation to ultimately produce a desired effect. The solidified particles range from being completely non-swellable to poorly swellable in a solvent from which protection is desired. The term "poorly swellable" refers to a particle that shows an increase in size relative to a non-swellable particle when placed in a solvent from which protection is desired.

In some embodiments, the substrate is capable of solidification, and may be in part or whole composed of various types of molecules: protein, carbohydrate, or synthetically derived molecules. The protein may be from the families of gelatins, collagens, or fibrins. The carbohydrate may be from the families of monosaccharides, disaccharides, oligosaccharides, and polysaccharides, with illustrative examples to include sucrose, trehalose, maltose, dextran, starch, alginates, xanthan, galactomanin, agar, or agarose. The synthetically derived molecule may be from the families of poly(ethylene glycol), poloxamer or polyesters. In some embodiments, the substrate may also include substances which do not inherently solidify, but may be needed to stabilize or aid the solidification process such as surfactants, stabilizers, emulsifiers, lyoprotectants, and cryoprotectants. Other processing aids may be helpful as well, for example in one embodiment cholesterol is used. Other types of component molecules that may be included in the substrate are agents that are intended to initiate and/or propagate and/or terminate the solidification process. In some embodiments, the agent is either slow initiating or may be externally initiated by means such as light irradiation, temperature, mechanical, pH change, etc.

In some embodiments, a mean hydrodynamic diameter of the particles, when in a solidified form, is less than 1 μm. In some embodiments, a mean hydrodynamic diameter of the particles, when in a solidified form, is greater than 1 μm.

In some embodiments, the particles may be either inherently or with help of an agent (i.e., surfactant, stabilizer, or emulsifier), mixed, or suspended within the solvent from which protection is desired. In some embodiments, the particles are incorporated into a polymer solution. In some embodiments, the polymer solution is extruded to create a fiber that is loaded with the target pharmaceutical or biological agent. In some embodiments, the polymer solution is three-dimensionally printed. In some embodiments, the surfactant, stabilizer, and emulsifier are incorporated into the substrate prior to solidification. In some embodiments, the surfactant, stabilizer, or emulsifier is incorporated with the substrate during or after solidification.

In some embodiments, the substrate is a mucopolysaccharide or a branched glucan.

In some embodiments, the substrate being solidified is a therapeutic protein and the solidification of the therapeutic protein alone provides protection from the solvent.

In some embodiments, the solidification process can proceed spontaneously through temperature-induced phase change. In some embodiments, the solidification process can proceed through addition of a cross-linking agent or other chemical entities that will ultimately initiate, propagate or otherwise aid in the solidification process, and wherein the cross-linking agent may be internally added to the solution that will become a dispersed phase of an emulsion once formed.

In other embodiments, the solidification process may occur because of dehydration, vitrification or crystallization of substrate that entraps the pharmaceutical or biological agent. Dehydration may occur at room temperature, elevated temperature or depressed temperature and in some cases, may be accompanied by vacuum applied to the suspension or mixture. In some cases, the dehydration may happen during a lyophilization process, where sublimation is used to remove some or all liquid components of the mixture or suspension, leaving behind the pharmaceutical or biological agent within lyophilized substrate. For liquid components of the mixture or suspension whose freezing point is below the capability of the lyophilization machine, these components will largely be removed by evaporation rather than sublimation.

DESCRIPTION

In this invention the terms "drug", "agent", "therapeutic agent", "biologically active agent" are collectively and synonymously defined to be compounds that based on structure or composition are expected to a) have physiological impact when introduced into a living organism, including human; or b) to act to catalyze or promote specific reactions that may or may not take place in a biological environment; for example, using enzymes in a non-biological environment to promote specific chiral chemistry. These compounds may be synthetically produced, or may be of biological origin, including by way of example: cells, viruses, proteins, peptides, oligonucleotides, all varieties of RNA and DNA, carbohydrates, lipids, etc.

There are numerous fields of medicine, pharmacology, as well as fields such as biotechnology, where the preservation of native confirmation/biological activity of an enzyme, therapeutic agent, or drug must be maintained during processes that involve exposure to organic solvents that might otherwise result in a decrease in their activity. To satisfy the need to preserve the potential activity of these therapeutic agents or drugs during the time when they are exposed to these solvents, a protective material may be used to isolate the drugs or therapeutic agents from this organic solvent environment without physically or chemically altering the agent itself. This protective material containing the drug may be mixed or suspended into the organic solvent of interest. There are numerous examples where this invention is needed; these are set forth as illustrative, and not meant to be comprehensive.

Fiber manufacturing using wet extrusion to create a drug-loaded fiber, textile or similar biomedical structure, is an example where, over the duration of the extrusion and until processes designed to remove residual solvent are completed, the drug must be protected from the solvent systems involved in the extrusion process. In this application, the choice of the materials used, and the choice of which type of condensation, gelling, or solidification method applied will also contribute to the rate at which drug is released from the fiber once the biomedical structure or device is in use.

Three-dimensional printing is another area where preservation of the native structure of a drug is desired. Similar to solvent exposure during an extrusion process, the drug must be protected while it is in the liquid (ink) form. This may require extremely long-term stability of the drug in solution, with months to even years of stability likely required in this application.

This invention relates to the composition of a protection matrix that may be used to encapsulate molecules that are sensitive to organic solvent exposure, wherein the encapsulating matrix mitigates damage to these molecules. There are numerous different materials that can be used as a protective matrix, including, in some cases, the drug itself. The essence of this invention is to identify the fundamental rules that must be followed to ensure that the drug of interest is likely to be protected. This invention also relates to the creation of a self-protection conformation for a given drug, wherein the drug is self-encapsulated and protected from the organic solvent. Some proteins, for example, can be reversibly precipitated to provide shielding from organic solvents.

The fundamental rules are as follows: The composition of substrate that is used to protect the drugs of interest must be soluble in a solution with the drugs to be protected. This solution may be composed of any fluids, salts, surfactants or stabilizers needed for the molecule of interest. It may also contain other additives as may be needed for processing steps, as will be illustrated in the various embodiments and examples to follow. This fluid must maintain the conformation of the drugs of interest or allow recovery to the conformation so that they can eventually perform their desired function.

The composition of substrate that is used to protect the drugs of interest must include components that are able to be cross-linked, gelled, vitrified, crystalized or by some means formed into particles that entrap or in some way contain and protect the drugs of interest.

The resulting particles used to protect the drugs of interest range from non-swellable to poorly swellable in the fluid from which protection is sought.

Any set of materials that meets all the above three rules or conditions and that is used for the specific purpose of protecting drugs from the presence of organic solvents is the topic of this invention. To meet most industrial and academic needs, it is usually desired that the particles are in the tens to thousands of nanometers diameter range.

As a practical matter of reduction to practice, it is usually required that the particles are suspendable within the organic solvent from which protection is sought. This ability to suspend these (typically nano-) particles is often achieved by associated surfactants. Suspension within the organic solvent of interest can also be achieved by particle interactions or the lack thereof (neutral surfaces). Surface surfactants provide sufficient organic interface to suspend these particles, and in many embodiments, reduce the aggregation potential of the particles. This typically results in a colloidal suspension, often visibly appearing as an opalescent suspension.

As this invention has been reduced to practice, there are many embodiments that will be illustrative of the process and teach the practice of creating these protection matrices. The embodiments provided within this specification are meant only to be illustrative, and do not represent an exhaustive list of applications of this invention.

In one embodiment, a water-in-oil micro or nanoemulsion is used to ensure that created particles are of a desired diameter, which is derived from the size of the dispersed aqueous phase in the emulsion. In this embodiment, a water phase of the emulsion contains the encapsulating substrate, the molecules to be protected, and any salts or stabilizers required by the molecules to be protected. The aqueous phase may often include a "water-side" surfactant to help stabilize the emulsion. If the encapsulating material performs its function of condensing, cross-linking, gelling, etc. as a result of a chemical reaction, that initiating chemical may also be present in the aqueous solution, potentially in an inactive state, or with a built-in delay. The oil phase of the emulsion will generally contain one or more surfactants. The oil phase may also contain chemicals that can act to initiate and/or propagate the condensing, cross-linking or gelling of the encapsulating material. Generally, the oil phase is chosen based upon the criteria of ease of removal and isolation of the formed encapsulating particles.

As a specific example of this embodiment, the molecule to be encapsulated is a therapeutic protein. The encapsulating material is gelatin, which will form a thermally-reversible "physical gel" when a solution of appropriate concentration is cooled. The organic phase is cyclohexane containing Span 80 (Sorbitan Monooleate). The aqueous phase contains the protein to be protected, Tween 80 (Polysorbate 80), and any salts or other stabilizers required of the protein. With appropriate ratios of Span 80, Tween 80, and organic to aqueous phases, a stable micro-emulsion or nano-emulsion can be formed. The aqueous phase in this emulsion consists of stable, isolated, dispersed droplets of water whose mean diameter is generally in the nanometer size. As gelatin thermally forms a gel upon cooling, the entire emulsion is slowly cooled. As the gelatin in each nano-droplet of water cools, it will begin to condense, thereby trapping the therapeutic protein and excess Tween 80 within each forming nanogel. As the cooling continues, the cyclohexane organic phase freezes. The cooling rate can then be dramatically accelerated to quickly freeze the water in the aqueous phase. Once all components are frozen, the entire emulsion can be lyophilized to remove both the cyclohexane as well as the water, ultimately leaving only the gelatin nanogels containing the therapeutic protein and surfactants.

This same system can use other materials as well, for example sodium alginate can be substituted for gelatin. In this embodiment, $CaCl_2$ is added to the cyclohexane. There is enough solubility of the $CaCl_2$ in this environment that the $Ca^{+2}$ ions are able to disperse throughout the emulsion, providing the ability to cross-link the alginate in the dispersed water phase.

The above two examples of thermal and chemical gelation serve as illustrations of reduction to practice of this embodiment of requirements one and two of this invention, i.e. that the encapsulating material (gelatin or alginate in the above examples) is soluble in the aqueous phase with the therapeutic protein as well as other molecules needed for processing, such as Tween 80. The second requirement is that the encapsulating material must be able to condense, gel, cross-link, vitrify, etc. The above two examples demonstrate two different mechanisms whereby this may take place. The third rule is that the encapsulating material must be very poorly swellable in the organic phase from which protection of the therapeutic protein is sought. This example illustrates how this concept can be tailor made for each situation. For example, gelatin is swellable and soluble in 1,1,1-3,3,3 hexafluoro-2 propanol, (HFIP) but not in dichloromethane (DCM). Therefore, if the solvent from protection is sought is HFIP, gelatin is a very poor choice, as the solvent will easily swell and penetrate the gelatin matrix and have full access to the therapeutic agent of interest, and thus violate rule three. However, if the solvent from which protection is sought is dichloromethane, gelatin is nearly completely insoluble in this material and will not significantly swell, nor will the solvent penetrate into the gelatin nanogels, thereby protecting the therapeutic protein of interest.

The above examples illustrate that if one knows which solvent(s) the molecules will be exposed to, it is possible, and very straight forward, to use the rules of this invention to design a system that will protect the molecules of interest.

WORKING EXAMPLES

Example 1

Dissolve 5% w/v gelatin in 10 mL Type I water in a scintillation vial by magnetically stirring at 37° C. for 1 hour. Weigh out a 3:1 mass/mass mixture of Span 80 and Tween 80 into a scintillation vial. When the gelatin has completely dissolved, add 1 mL of this warm solution to a vial containing lyophilized growth factor and allow to dissolve. Maintain at 37° C. Add 15 mL of dry cyclohexane to the scintillation vial. Vortex the scintillation vial to incorporate the surfactants into the cyclohexane. Place a vial into the chilled water bath and, while sonicating, slowly add the gelatin solution/growth factor drop-by-drop using a pipette. When complete, immediately place the vessel into an environmental chamber at 8° C. and set the mixer plate to rotate at a speed of 35/70 for a minimum of 60 minutes to gel the gelatin. A water-soluble, non-toxic cross-linking system, such as N-hydroxysuccinimide (NHS) and 1-(3-dimethyl-aminopropyl)-3-ethyl-carbodiimide hydrochloride (CDI) can be incorporated into the process to further condense and solidify the gelatin nanoparticles. Snap freeze and lyophilize the solution at the completion of gelation.

Example 2

Substitute sodium alginate for gelatin in Example 1 and add measured quantity of $CaCl_2$ to the formed emulsion to yield a 40 mM solution with respect to the aqueous portion in order to gel the alginate. The NHS and CDI are also omitted. Freeze and lyophilize the emulsion following gelation of the alginate.

Example 3

In a scintillation vial, create a dextran solution in type I water at 6% w/vol. In another scintillation vial, weigh an appropriate mass of Tween 80 to yield a solution at 0.058 g/ml in the dextran solution. Mix appropriately. Weigh out lysozyme to be dissolved in 3.0 mL of the dextran/T80 solution to yield the final desired concentration. Transfer the appropriate volume into the scintillation vial containing lysozyme to create a 0.003 g/mL solution. Weight Span 80 into a 45 mL scintillation vial. Add an appropriate volume of filtered cyclohexane to the vial to obtain a final solution concentration of 0.0118 g/mL of the desired volume. Vortex to incorporate the surfactant. Place the cyclohexane/Span vial into a chilled water bath and immerse a sonicator probe. While sonicating, add the desired volume of the dextran 70/Tween 80/lysozyme solution to the cyclohexane/Span 80, drop-by-drop, to emulsify. Place the vial into a freezer at −20° C. and allow to slow freeze for a minimum of four hours, preferably overnight, to freeze the free-water in the dextran/lysozyme dispersed aqueous phase. Lyophilize the frozen emulsion upon completion.

Example 4

To a measured quantity of lysozyme, add 0.020 g of poloxamer P188 surfactant. Solubilize in Type I water at approximately 75 mg/mL. Add 0.96 g of PLGA to a tall scintillation vial and dissolve with 16 mL of filtered acetone. Maintain vessel temperature at 25° C. While stirring, add 500 μL aliquots of acetone slowly into the lysozyme solution until 2.5 mL have been added. Cap the vessel and hold for 60 seconds. Repeat the additions until approximately 5 mL have been added to the vessel. Cap and hold another 60 seconds. Switch to 100 μL aliquots of acetone and add while stirring. Cap the vessel and hold between additions for 30 seconds. Continue to add acetone until the solution turns and remains opalescent, indicating the protein has nanoprecipitated. Cap the vessel and stir for five minutes. Add a stir bar to the polymer solution and add the nanoprecipitate solution into the polymer solution in small aliquots. When complete, stir for an additional 5 minutes. The resultant solution should be opalescent and stable. Place a beaker containing 500 mL of pentane into a sonic water bath. Syringe deliver the polymer solution into the pentane bath, while sonicating, via a small diameter blunt needle at no more than 0.5 ml/min. When delivery is complete, allow the material to sit statically in pentane for 30 minutes to solidify the polymer. Pour off/pipette off the pentane and transfer the material into a small lyophilization vessel. Place the vessel into a vacuum oven at 37° C. for three hours (maximum vacuum) to extract the residual pentane. Prepare a dry ice/pentane bath, snap freeze the material for 15 minutes, and then lyophilize to remove residual water and solvent. Store appropriately.

Example 5

Prepare a DCM/Span 80 solution at 0.0045 g/mL, and a 3% Tween 80 solution in type I water. Solubilize lidocaine HCL in the Tween solution at the desired concentration. Prepare a 7.5% wt/v PLLA solution in dichloromethane/Span 80 using high molecular weight polymer. When complete, pipette 500 μL of the prepared lidocaine HCL/Tween 80 solution into the polymer solution to create a primary emulsion. Emulsify according to standard practice, preferably using pulsed sonication. Load the emulsion into a 10 mL rubber-free syringe, attach a small diameter blunt needle, and deliver the contents at a rate of 0.150 mL/min, 5 inches above a vessel containing approximately 600 mL of pentane. The vessel also contains a filter screen or basket to capture formed particles. When solution delivery is complete, wait 30 minutes to allow for particle solidification, and then transfer the particles into a lyophilization flask. Place the flask into a vacuum oven at 37° C. and allow the particles to dry for three hours. Load the particles into a scintillation vial or similar vessel, and immerse the vial into a pentane/dry ice bath to freeze the material. Lyophilize for a minimum of 24 hours to remove residual water and pentane.

Example 6

Prepare 30.0 ml of 0.4M AOT/isooctane volumetrically using a 50 ml centrifuge tube. Create a solution of PEGylated alginate at 74 mg/ml in pure water. Prepare $CaCl_2$ solution at a concentration of 110 mM in filtered nanopure water. Dissolve BSA at a concentration of 7.33 mg/ml in filtered, nanopure water. Load 0.77 ml of PEGylated alginate solution into a 3 ml disposable syringe (A). Load 0.33 ml of BSA solution into another 3 ml disposable syringe (B), and load 0.11 ml of $CaCl_2$ solution into syringe a third syringe (C). Connect syringes A&B and mix the two solutions by moving the material from one syringe to the other 20 times. Separate the two syringes and connect a new (D) 3 ml disposable syringe to the syringe containing the mixed material. Push the PEGylated alginate/BSA solution into the new syringe through a 0.2 μm filter. Dispose of the empty syringe and filter. Empty the syringe containing of filtered PEGylated alginate into a 1.5 mL centrifuge tube. Withdraw 1.000 ml from the Eppendorf, and pipette it into the vial containing the lyophilized protein to be loaded. Mix well, but do not vortex the material. Connect a sterile needle to syringe D and carefully withdraw the fluid from the vial containing the protein. Connect syringe D to syringe C, which contains $CaCl_2$ solution. Push the PEGylated alginate/BSA/protein into the $CaCl_2$ solution, then syringe back and forth 20 times to ensure that the $Ca^{2+}$ is well dispersed. Immediately empty the syringe contents into previously prepared 20.9 ml of 0.4M AOT/isooctane in a 50 ml centrifuge tube. Cap the tube and vortex. Place the tube vertically in the refrigerator at 4° C. immediately after vortexing. Allow to gel overnight. Lightly centrifuge the tube at 1500 rpm for 15 minutes. Discard the supernatant without disturbing the pellet and then wash the retained material three times with ethanol. Remove/evaporate the ethanol and store the resulting material for use.

Example 7

Create a dextran/lysozyme solution in nanopure water, with dextran 70 at 6% w/w, and with lysozyme added at 2 mg/mL. Create a PEG 8000 solution at 6% w/w. Create a 1:10 w/w blend of the dextran 70/lysozyme:PEG 8000 solutions and vortex to blend. These ratios should allow for the creation of a single phase aqueous system. Place the solutions in the freezer at −20° C. for at least 8 hours to slow freeze and phase separate into a water-in-water emulsion. Snap freeze and lyophilize the vial for 48 hours, minimum. When complete, add 10 mL dichloromethane to the tube, vortex, and then centrifuge for 15 minutes to collect the formed dextran particles. Discard the supernatant, refill with DCM, and centrifuge again. Repeat this washing process a total of three times. Dry the tubes for at least 8 hours in a vacuum oven at RT and maximum vacuum.

Example 8

As in the previous example, create a 1:10 w/w blend of dextran 70/PEG 8000 solution containing a protein of interest. Spray atomize the single-phase solution into liquid nitrogen to create ice particles of PEG/dextran/protein that are sub-25 μm. Collect the particles while frozen and disperse into a vessel of cyclohexane chilled to 7° C. The frozen dextran/PEG/protein particles should locally freeze the cyclohexane, which has a freezing temperature of approximately 6.5° C., and remain dispersed. Immediately hard freeze the suspension in dry ice/pentane, and then allow the frozen material to return to 4° C. to thaw the aqueous portion but maintain the cyclohexane in a frozen state. Hold at this temperature for an hour, and then transfer the material to a −20° C. freezer for at least 8 hours to invoke temperature-induced phase separation of the dextran/PEG and vitrification of the dextran. The resultant glassy dextran will encapsulate and protect the protein. Hard freeze in dry ice/pentane, and then lyophilize to recover particles. Wash with DCM repeatedly to remove PEG.

Example 9

Create a solution of dextran 70 containing a protein of interest. Using a sonic atomizer, spray atomize the solution into liquid nitrogen to create ice particles of dextran that are sub-20 μm. Collect the particles while frozen and disperse into a vessel of cyclohexane chilled to 7° C. The frozen dextran/protein particles should locally freeze the cyclohexane, which has a freezing temperature of approximately 6.5° C., and remain dispersed. Immediately hard freeze the suspension in dry ice/pentane, and then allow the frozen material to return to 4° C. to thaw the aqueous portion but maintain the cyclohexane in a frozen state. Hold at this temperature for an hour, and then transfer the material to a −20° C. freezer for at least 8 hours to invoke temperature-induced vitrification of the dextran. The resultant glassy dextran will encapsulate and protect the protein. Hard freeze in dry ice/pentane, and then lyophilize to recover particles.

Example 10

Create a solution of dextran 70 at 10% w/vol in a scintillation vial and allow to solubilize at 37° C. for 30 minutes. Weigh trehalose into a scintillation vial to obtain a desired end concentration of 10% w/vol. Add an appropriate volume of the dextran solution to this vial and allow to solubilize. Measure Tween 80 into a scintillation vial to obtain the desired final volume at a concentration of 5.8% wt/vol. Add the dextran/trehalose solution to this to obtain the desired volume of aqueous solution. Prepare a Span 80/cycloheptane solution at 1.18% w/vol. To a vial containing 1 mg/mL protein, add 500 μL of the prepared aqueous solution. Mix gently to incorporate. Pipette this solution into a vial containing 7.5 mL of the cycloheptane/Span 80 solution and emulsify to create a nano-size colloidal suspension. Transfer the emulsion to a 20 mL lyophilization vial and place onto a shelf that has been pre-cooled to −55° C. Allow to freeze for 2 hours. Lyophilize the material to recover the lyocake containing nanoparticles of protein encapsulated in trehalose/dextran.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A liquid ink composition configured for three-dimensional printing comprising:

a liquid phase comprising a polymer, and particles, poorly swellable in the liquid phase, suspended in the liquid phase, the particles containing an active pharmaceutical or biological agent in a native configuration with preserved biological activity wherein the liquid phase is configured to solidify to form a three dimensional structure, and wherein the biological activity of the pharmaceutical or biological agent is preserved upon solidification of the liquid phase.

2. The liquid ink composition of claim 1, the particles being formed by a process comprising:

preparing a solution, formed from water as a solvent, comprising:

(a) the pharmaceutical or a biological agent; and (b) a substrate that is soluble in the solution, the substrate comprising one or more chemical species;

combining the solution with an oil phase to form a water-in-oil emulsion in which the solution is dispersed in the oil phase;

lyophilizing the emulsion, wherein:

(i) the particles are formed prior to or simultaneously with the lyophilizing, (ii) the pharmaceutical or biological agent is entrapped by the particles, (iii) the substrate and the oil phase are selected so that the particles formed are suspendable in the liquid composition and the biological activity of the pharmaceutical or biological agent is preserved upon suspension of the particles in the liquid composition, and (iv) the substrate comprises a substance selected from the group consisting of a surfactant, a stabilizer, an emulsifier, and combinations thereof.

3. A method of forming a liquid composition configured for three-dimensional printing comprising:

preparing a solidifiable composition comprising:

(i) a solution containing a pharmaceutical or biological agent having biological activity; and (ii) a substrate that is soluble in the solution, the substrate comprising components capable of being solidified via a solidification process selected from the group consisting of vitrification, crystallization, physical cross-linking, chemical cross-linking, and combinations thereof;

solidifying the solidifiable composition by means of the solidification process, thereby forming particles, after or as a result of the solidification process, comprising the pharmaceutical or biological agent, wherein the biological activity of the pharmaceutical or biological agent and is preserved during the forming of the particles; and suspending the particles in a liquid phase comprising a polymer, the liquid phase being configured to solidify, wherein the biological activity of the pharmaceutical or biological agent, comprised by the particles, is preserved upon forming the liquid composition, and upon solidification of the liquid phase.

* * * * *